(12) United States Patent
Erker et al.

(10) Patent No.: US 6,809,211 B2
(45) Date of Patent: Oct. 26, 2004

(54) CATALYSTS FOR POLYMERIZATION OF ALKYLENE OXIDES

(75) Inventors: Gerhard Erker, Münster (DE); Alexander Snell, Altötting (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/419,583

(22) Filed: Apr. 21, 2003

(65) Prior Publication Data

US 2004/0010165 A1 Jan. 15, 2004

(30) Foreign Application Priority Data

Apr. 26, 2002 (DE) .......................................... 102 18 583

(51) Int. Cl.$^7$ ............................ C07F 7/00; B01J 31/00; C08F 34/02
(52) U.S. Cl. ........................... 556/54; 556/56; 556/130; 556/135; 556/182; 502/171; 526/266; 526/273
(58) Field of Search ............................ 556/54, 56, 130, 556/135, 182; 502/171; 526/266, 273

(56) References Cited

U.S. PATENT DOCUMENTS

| | | | |
|---|---|---|---|
| 3,404,109 A | 10/1968 | Milgrom | 260/611 |
| 3,829,505 A | 8/1974 | Herold | 260/611 B |
| 3,941,849 A | 3/1976 | Herold | 260/607 A |
| 4,654,417 A | 3/1987 | Inoue et al. | 528/416 |
| 5,158,922 A | 10/1992 | Hinney et al. | 502/175 |
| 5,328,970 A | 7/1994 | Inoue et al. | 526/161 |
| 5,470,813 A | 11/1995 | Le-Khac | 502/175 |

OTHER PUBLICATIONS

F. Teixidor, A. Liobet, L. Esriche, J. Casabo: Polyhedron, Bd. 4, Nr. 2, 1985, Seiten 215–219, XP008021942 das ganze dokument.

F. Teixidor, F. Flor, J. Casabo: Inorg. Chim. Acta, Bd. 118, 1986, Seiten 125–128, XP008021940 das ganze dokument.

J. Casabo, J. Colomer, L. Escriche, F. Teixidor, E. Molins, C. Miravitlles: Inorg. Chim. Acta, Bd. 178, 1990, Seiten 221–226, XP008021939 das ganze dokument.

F. Teixidor, A. Liobet, L. Escriche, J. Casabo: Polyhedron, Bd. 3, 1984, Seiten 1017–1019, XP008021941 das ganze Dokument.

Snell, Alexander H.: "Neuartige Gruppe–4–Metallkomplexe für die Polymerisation von polaren und Unpolaren Monomeren, Dissertation Universität Münster" Jun. 24, 2002, Miami, Universitäts–Und Landesbibliothek Münster XP002255161 Seite 6–27 Seite 55–69.

*Primary Examiner*—Porfirio Nazario-Gonzalez
(74) *Attorney, Agent, or Firm*—Joseph C. Gil; John E. Mrozinski, Jr.

(57) ABSTRACT

The present invention provides new coordinative catalysts for the polymerization of alkylene oxides.

5 Claims, No Drawings

CATALYSTS FOR POLYMERIZATION OF ALKYLENE OXIDES

FIELD OF THE INVENTION

The present invention provides new coordinative catalysts for polymerization of alkylene oxides.

BACKGROUND OF THE INVENTION

Polyalkylene oxides which are obtainable by polymerization of alkylene oxides, e.g. ethylene oxide, propylene oxide or 1,2-butylene oxide, are used commercially in a number of applications such as non-ionic surfactants, lubricants, braking fluids or hydraulic fluids. If the alkylene oxides are polymerized in the presence of starter compounds with active hydrogen atoms, polyether polyols are obtained, and these are used widely for producing polyurethane materials such as paints, sealants, elastomers or foams.

Polymerization of alkylene oxides may be catalyzed by a basic, acid or coordinative mechanism. The basic catalysts employed in industry for polymerization of alkylene oxides are chiefly caustic alkalis (e.g. KOH). The disadvantages of polymerization catalyzed by caustic alkalis are the long reaction times and the very expensive processing of the product to separate the basic catalyst. Another problem is the transposition of alkylene oxides such as propylene oxide with a basic catalyst to form allyl or propenyl alcohols, which takes place as a side reaction, the alcohols giving monofunctional, unsaturated polyethers with a double bond on the end, so-called monols, in the production of polyether polyol. Since the proportion of monool increases greatly as the molar weight of polyether rises, the equivalent molar weight (numerical mean molar weight/functionality) is limited to about 2000 g/mol in polyether polyol production by means of KOH catalysis.

As well as basic catalysis, acid catalysis, particularly with Lewis acids e.g. boron trifluoride, has long been known for polymerization of alkylene oxides. The drawback of acid catalysis is that it further encourages side reactions (e.g. formation of volatile, low molecular weight cyclic ethers such as dioxans or dioxolans), so generally speaking only products with numerical mean molar weights up to about 1000 g/mol can be obtained, and molar weight distribution in polyalkylene oxides is wider than in products made by basic catalysis.

Coordinative catalysts for polymerization of alkylene oxides have also been known for quite a long time. The first catalysts described for coordinative polymerization of alkylene oxides were iron chloride, diethyl zinc and various trialkylaluminium compounds with additives and co-catalysts. The disadvantages of these first coordinative catalysts for alkylene oxide polymerization were their relatively low activity and the difficulty of separating them from the product. As chain exchange between the growing polyalkylene oxide chain and an added starter compound is very slow with these catalyst systems, the molar weight of the polymers and often also the end group functionality cannot be effectively controlled, which makes the products unsuitable for polyurethane applications. In addition, these catalyst systems produce parts of stereoregular polyethers in some cases.

Porphyrin complexes of aluminum, zinc and manganese also catalyze polymerization of alkylene oxides by a coordinative mechanism (see e.g. EP-A 195 951, EP-A 510 602, U.S. Pat. No. 5,328,970). The polyalkylene oxides obtained are atactic and have a narrow molar weight distribution. A general problem with the use of these metalloporphyrin complexes, however, is completely separating the strongly colored catalyst systems from the product. As the catalysts are also very expensive to prepare, metalloporphyrins are unsuitable for producing polyalkylene oxides on an industrial scale for economic reasons.

Double metal cyanide (DMC) catalysts based on zinc hexacyanocobaltate, when modified by suitable organic complex ligands, are very effective catalysts for coordinative alkylene oxide polymerization (see e.g. U.S. Pat. Nos. 3,404,109, 3,829,505, 3,941,849, 5,158,922, 5,470,813). Atactic polyalkylene oxides with very narrow molar weight distributions and an extremely low content of unsaturated by-products are obtained by employing highly active DMC catalysts. DMC catalysts however have the disadvantage of not allowing controlled polymerization of ethylene oxide and hence also not allowing production of polyethylene oxides or polyalkylene oxide block copolymers with ethylene oxide blocks. In addition, the induction period characteristic of DMC catalysis at the beginning of polymerization frequently causes processing problems, particularly in large-scale industrial processes.

Improved catalyst systems for coordinative polymerization of alkylene oxides leading to atactic polyalkylene oxides with a narrow molar weight distribution and low proportions of unsaturated by-products are therefore of great interest.

DETAILED DESCRIPTION OF THE INVENTION

The present invention will now be described for purposes of illustration and not limitation.

Certain novel metal complex compounds have been found to be very effective catalysts for coordinative polymerization of alkylene oxides, which are used to Obtain atactic polyalkylene oxides with narrow molar weight distributions and a very low content of undesirable by-products. Alkylene oxide polymerization with these new coordinative catalysts takes place without an induction period and can therefore be carried out without any processing problems.

The subject of the present invention is thus new coordinative catalysts for alkylene oxide polymerization, of general formula (I)

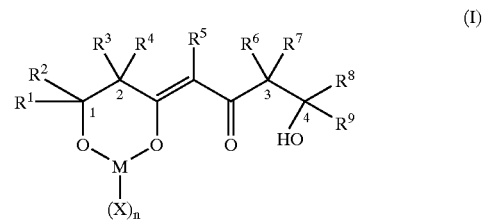

wherein $R^1$–$R^9$ independently represent H, a substituted or unsubstituted, straight or branched $C_1$–$C_{20}$ alkyl group, a substituted or unsubstituted $C_5$–$C_{20}$ aryl group, a substituted or unsubstituted $C_5$–$C_{20}$ aralkyl group, an acyl group, an alkoxide group, F, Cl, Br, I, CN or $NO_2$. $R^1$ to $R^4$ and $R^6$ to $R^9$ may also form aromatic ring systems together with C1 and C2 and, respectively, C3 and C4. $R^2$ and $R^3$ and, respectively, $R^7$ and $R^8$ may also be components of a $C_3$–$C_{20}$ cycloaliphatic ring system e.g. cyclohexyl.

M represents a metal at oxidation stage II–VII.

X represents F, Cl, Br, I, H, CN, a substituted or unsubstituted, straight or branched C1–C20 alkyl group, a substituted or unsubstituted $C_5$–$C_{20}$ aryl group, a substituted or unsubstituted $C_5$–$C_{20}$ aralkyl group, an acyl group, an alkoxide group, a thiolate group or a dialkylamino group. Two or more of the X groups may optionally be bridged, preferably with an alkylene bridge. For n is at least 2, the X groups may be the same or different. X is preferably F, Cl, Br or I and particularly preferably Cl.

n represents 0, 1, 2, 3, 4 or 5 and is chosen to maintain the electric neutrality of the metal complex compound.

If M is at oxidation stage II, then n=0. Some examples are Sn(II), PB(II), Zn(II), Cd(II), Hg(II), Fe(II), Co(II), Ni(II), Ca(II), Sr(II), Ba(II), Cr(II), Mn(II), Cu(II), Pd(II), Pt(II) and V(II).

If M is at oxidation stage III, then n=0. Some examples are Al(III), Ti(III), Co(III), Fe(III), Au(III), V(III), Cr(III), Sc(III), Y(III), La(III), Ce(III), Pr(III), Nd(III), Sm(III), Eu(III), Gd(III), Tb(III), Dy(III), Ho(III), Er(III), Tm(III), Yb(III) and Lu(III).

If M is at oxidation stage IV, then n=2. Some examples are Ti(IV), Zr(IV), Hf(IV), Sn(IV), Mo(IV), V(IV) and W(IV).

If M is at oxidation stage V, then n=3. Some examples are V(V), Nb(V) and Ta(V).

If M is at oxidation stage VI, then n=4. Some examples are Cr(VI), Mo(VI), W(VI) and Re(VI).

If M is at oxidation stage VII, then n=5. Some examples are Tc(VII) and Re(VII).

It is preferable to use metal complex compounds of general formula (I) with metals M at oxidation stage II, III and IV. Zn(II), Al(III), Ti(IV), Zr(IV) and HF(IV) are particularly preferred.

The preferred catalyst systems are those in which C1 and C2 and, respectively, C3 and C4 in formula (I) are each components of an aromatic ring system, e.g. of a phenyl, naphthyl, pyridyl or thiophenyl ring. Catalyst systems of general formula (II) are particularly preferred

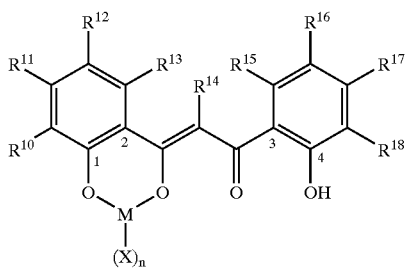

(II)

wherein $R^{10}$–$R^{18}$ may be the same or different radicals and, independently of each other, are H, a substituted or unsubstituted, straight or branched $C_1$–$C_{20}$ alkyl group, a substituted or unsubstituted $C_5$–$C_{20}$ aryl group, a substituted or unsubstituted $C_5$–$C_{20}$ aralkyl group, an acyl group, an alkoxide group, a thiolate group, F, Cl, Br, I, CN, $NO_2$ or constituents of partially condensed cycloaliphatic or aromatic ring systems with 3–20 C atoms. $R^{10}$ to $R^{18}$ are preferably H, straight or branched $C_1$–$C_6$ alkyl groups, F, Cl, Br, I or constituents of partially condensed cycloaliphatic or aromatic ring systems with 3–15 carbon atoms.

M, X and n have the meaning defined in formula (I). Compounds containing metals M at oxidation stage II, III and IV are preferred, particularly preferably those in which M is Zn(II), Al(III), Ti(IV), Zr(IV) or Hf(IV). X is preferably F, Cl, Br or I, particularly preferably Cl.

The catalysts are generally synthesized in a simple manner by reacting suitable metal compounds (e.g. titanium tetrachloride for M=Ti(IV), n=2 and X=Cl in formula (II), with ligand precursors (e.g. 1,3-bis(2-hydroxyphenyl)-1,3-propane dione for $R^{10}$–$R^{18}$=H in formula (II)).

The catalysts according to the invention are used for coordinative polymerization of alkylene oxides.

Some examples of suitable alkylene oxides are ethylene oxide, propylene oxide, 1,2-butylene oxide, 2,3-butylene oxide, styrene oxide, vinyloxiran, glycidol, allylglycidyl ethers and mixtures thereof. The polyether chains may be built up by alkoxylation with only one monomeric alkylene oxide or also randomly or block by block with two or more different monomeric alkylene oxides. It is preferable to use ethylene oxide, propylene oxide, 1,2-butylene oxide, 2,3-butylene oxide or mixtures thereof.

The alkylene oxides are optionally polymerized in the presence of starter compounds with active hydrogen atoms. Polyether polyols suitable for producing polyurethane materials are obtained in this way. The starter compounds with active hydrogen atoms which are used are compounds with molecular weights of 18 to 1000 and 1 to 8 hydroxyl, thiol and/or amino groups. Some examples are ethylene glycol, diethylene glycol, triethylene glycol, 1,2-propylene glycol, 1,4-butane diol, hexamethylene glycol, bisphenol A, trimethylene propane, glycerin, pentaerythritol, sorbitol, cane sugar, degraded starch, water, methylamine, ethyl amine, propylamine, butylamine, aniline, benzylamine, o- or p-toluidine, α,β-naphthylamine, ammonia, ethylene diamine, propylene diamine, 1,4-butylene diamine, 1,2-, 1,3-, 1,4-, 1,5- or 1,6-hexamethylene diamine, o-, m- or p-phenylene diamine, 2,2'-, 2,4'- or 4,4'-diaminodiphenylmethane or diethylene diamine.

Polymerization of alkylene oxides catalyzed by the catalysts according to the invention generally takes place at temperatures from –20 to 200° C., preferably 0 to 180° C. and particularly preferably 20 to 160° C. The reaction may be carried out at total pressures from 0.001 to 20 bar. Polymerization may be carried out in substance or in an inert organic solvent such as cyclohexane, toluene, xylene, tetrahydrofurane, diethylether, dimethoxyethane, dioxane and/or chlorinated hydrocarbons such as methylene chloride, chloroform or 1,2-dichloropropane. The quantity of solvent is usually 10 to 30% by weight relative to the quantity of polyalkylene oxide to be prepared.

The concentration of catalyst is chosen so that good control of the polymerization reaction is possible under the given reaction conditions. The concentration of catalyst is generally 0.001% to 2% by weight, preferably 0.01 to 1.5% and particularly preferably 0.1 to 1% relative to the quantity of polyalkylene oxide to be prepared.

The reaction times are from a few minutes to several hours. Polyalkoxylation may be carried out continuously or in a batch or semi-batch process.

The (numerical mean) molecular weights of the polyalkylene oxides prepared with the catalysts according to the invention are 200 to 500000 g/mol, preferably 500 to 50000 g/mol and particularly preferably 1000 to 20000 g/mol. The polyalkylene oxides prepared with the catalysts according to the invention are characterized by narrow molar weight distributions and low polydispersivities ($M_w/M_n$). The polydispersivities are generally less than 1.5 and preferably less than 1.2. The molar weight values and polydispersivities are usually determined by gel permeation chromatography (GPC) calibrated with appropriate polyalkylene oxide standards.

Polymerization of propylene oxide with the catalysts according to the invention produces atactic polypropylene oxides. The tacticity is usually determined by $^{13}$C-NMR spectroscopy.

The invention is further illustrated but is not intended to be limited by the following examples in which all parts and percentages are by weight unless otherwise specified.

EXAMPLES

Example A

Catalyst Synthesis

Preparation of 1-(2-phenolato-3-(2-hydroxyphenyl)-propane-3-one-1-onatotitanium dichloride (catalyst A)

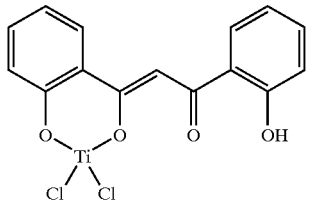

285 mg (1.50 mmol) titanium tetrachloride was dissolved in 10 ml dichloromethane in an inert gas (argon) and mixed with 384 mg (1.50 mmol) 1,3-bis(2-hydroxyphenyl)-1,3-propane dione at room temperature. After only a few minutes, a red deposit formed. This was allowed to react for two hours, filtered off, washed with a small quantity of pentane and dried under a hydraulic pump vacuum.

Yield: 524 mg (1.40 mmol, 94%)

Examples 1–9

Preparation of Polypropylene Oxides 37.3 mg (0.10 mmol) of catalyst A was weighed into a Schlenk vessel in an inert gas (argon) and then mixed with 8.3 g (143 mmol) propylene oxide at room temperature by means of a syringe. The polymerization batch was then stirred under argon at room temperature for a defined period. When the reaction time had elapsed, non-reacted propylene oxide was removed in a hydraulic pump vacuum. Highly viscous, oil-like liquids were obtained and were characterized without separating the catalyst. The results are summarized in Table 1.

TABLE 1

Polymerization of propylene oxide with catalyst A

| Ex. | Time [h] | Yield [g] | Conversion [%] | $M_n$ [g/mol]$^a$ | $M_w$ [g/mol]$^a$ | $M_w/M_n{}^a$ |
|---|---|---|---|---|---|---|
| 1 | 0.5 | 3.48 | 41.9 | 9823 | 10601 | 1.0793 |
| 2 | 1 | 4.04 | 48.6 | 10796 | 11555 | 1.0703 |
| 3 | 2 | 4.69 | 56.5 | 12963 | 13917 | 1.0736 |
| 4 | 3 | 5.02 | 60.5 | 11863 | 12737 | 1.0736 |
| 5 | 4 | 5.43 | 65.4 | 12047 | 12922 | 1.0726 |
| 6 | 5 | 5.79 | 69.8 | 12342 | 13281 | 1.0760 |
| 7 | 6 | 6.06 | 73.0 | 12525 | 13357 | 1.0664 |
| 8 | 15 | 6.52 | 78.6 | 13324 | 14213 | 1.0667 |
| 9 | 48 | 7.13 | 85.9 | 14340 | 15440 | 1.0767 |

$^a$determined by GPC (eluant THF, calibration with polypropylene oxide standards)

The polypropylene oxides obtained with catalyst A have relatively high numerical mean molar weights with values between approx. 10000 and 15000 g/mol and very narrow molar weight distributions with poly-dispersivities $M_w/M_n<1.08$.

The polypropylene oxide from Example 2 was additionally examined by $^{13}$C-NMR spectroscopy. $^{13}$C-NMR analysis showed it to be an atactic product with random distribution of isotactic and syndiotactic diads. No by-products characteristic of basic or acid catalysis were detected.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A catalyst of the formula (I)

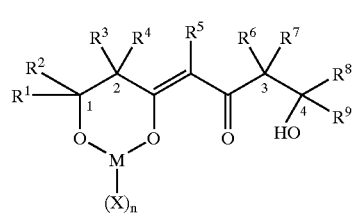

wherein $R^1$–$R^9$, independently represent H, a substituted or unsubstituted, straight or branched $C_1$–$C_{20}$ alkyl group, a substituted or unsubstituted $C_5$–$C_{20}$ aryl group, a substituted or unsubstituted $C_5$–$C_{20}$ aralkyl group, an acyl group, an alkoxide group, F, Cl, Br, I, CN or $NO_2$, or $R^2$ and $R^3$ and/or $R^7$ and $R^8$ together form a partially condensed $C_3$–$C_{20}$ cycloaliphatic ring system, or $R^1$ to $R^4$ and/or $R^6$ to $R^9$ together form a partially condensed aromatic ring system;

M represents a metal at oxidation stage II–VII;

X represents F, Cl, Br, I, H, CN, a substituted or unsubstituted, straight or branched $C_1$–$C_{20}$ alkyl group, a substituted or unsubstituted $C_5$–$C_{20}$ aryl group, a substituted or unsubstituted $C_5$–$C_{20}$ aralkyl group, an acyl group, an alkoxide group, a thiolate group or a dialkylamino group;

n represents 0, 1, 2, 3, 4 or 5 and is chosen to maintain the electric neutrality of the metal complex compound.

2. A catalyst of the formula (II)

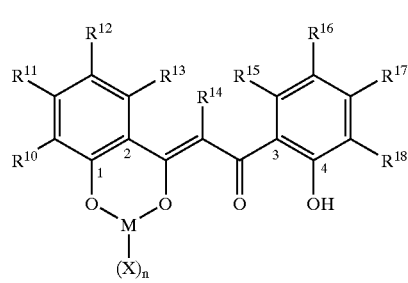

wherein $R^{10}$–$R^{18}$, independently represent H, a substituted or unsubstituted, straight or branched $C_1$–$C_{20}$ alkyl group, a substituted or unsubstituted $C_5$–$C_{20}$ aryl group, a substituted or unsubstituted $C_5$–$C_{20}$ aralkyl group, an acyl group, an alkoxide group, a thiolate group, F, Cl, Br, I, CN, $NO_2$ or constituents of partially condensed cycloaliphatic or aromatic ring systems with 3–20 carbon atoms;

M represents a metal at oxidation stage II–VII;

X represents F, Cl, Br, I, H, CN, a substituted or unsubstituted, straight or branched $C_1$–$C_{20}$ alkyl group, a substituted or unsubstituted $C_5$–$C_{20}$ aryl group, a substituted or unsubstituted $C_5$–$C_{20}$ aralkyl group, an acyl group, an alkoxide group, a thiolate group or a dialkylamino group;

n represents 0, 1, 2, 3, 4 or 5 and is chosen to maintain the electric neutrality of the metal complex compound.

3. The catalyst according to claim 2, wherein $R^{10}$ to $R^{18}$, independently represent H, straight or branched $C_1$–$C_6$ alkyl groups, F, Cl, Br, I or constituents of partially condensed cycloaliphatic or aromatic ring systems with 3–15 carbon atoms;

M represents Zn(II), Al(III), Ti(IV), Zr(IV) or Hf(IV);

X represents F, Cl, Br or I.

4. A method of making a polyalkylene oxide comprising polymerizing an alkylene oxide in the presence of a catalyst according to claim 1 and collecting the product.

5. A method of making a polyalkylene oxide comprising polymerizing an alkylene oxide in the presence of a catalyst according to claim 2 and collecting the product.

* * * * *